(12) United States Patent
Park et al.

(10) Patent No.: US 7,314,447 B2
(45) Date of Patent: Jan. 1, 2008

(54) SYSTEM AND METHOD FOR ACTIVELY COOLING TRANSDUCER ASSEMBLY ELECTRONICS

(75) Inventors: William J. Park, San Jose, CA (US); Vaughn Marian, Saratoga, CA (US); David Petersen, Fall City, WA (US); Todor Sheljaskow, Issaquah, WA (US); Mirsaid S. Boloforosh, Portola Valley, CA (US); Worth B. Walters, Cupertino, CA (US); Sevig Ayter, Cupertino, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 265 days.

(21) Appl. No.: 10/800,950

(22) Filed: Mar. 15, 2004
(Under 37 CFR 1.47)

(65) Prior Publication Data
US 2005/0075573 A1    Apr. 7, 2005

Related U.S. Application Data

(63) Continuation-in-part of application No. 10/183,302, filed on Jun. 27, 2002.

(51) Int. Cl.
*A61B 8/00* (2006.01)

(52) U.S. Cl. .................................................... 600/459

(58) Field of Classification Search ................ 600/437, 600/443, 459–471
See application file for complete search history.

(56) References Cited

U.S. PATENT DOCUMENTS

| | | | |
|---|---|---|---|
| 3,573,557 A * | 4/1971 | Riggs | 361/700 |
| 4,567,895 A | 2/1986 | Putzke | 128/660 |
| 4,672,972 A * | 6/1987 | Berke | 600/422 |
| 5,047,637 A * | 9/1991 | Toda | 250/306 |
| 5,213,103 A * | 5/1993 | Martin et al. | 600/443 |
| 5,307,813 A * | 5/1994 | Young | 600/420 |
| 5,545,942 A | 8/1996 | Jaster et al. | 310/341 |
| 5,560,362 A | 10/1996 | Sliwa, Jr. et al. | 128/660.03 |
| 5,690,114 A | 11/1997 | Chiang et al. | 128/661.01 |
| 5,721,463 A | 2/1998 | Snyder | 310/334 |

(Continued)

FOREIGN PATENT DOCUMENTS

JP       404336052    * 11/1992    ................ 600/459

(Continued)

OTHER PUBLICATIONS

Robert E. Simons, electronics cooling applications article "Electronics Cooling: Direct liquid immersion cooling for high power density microelectronics" obtained at http://www.electronics-cooling.com/Resources/EC_Articles/May96/may96_04.htm, pp. 1-9, Feb. 13, 2004.

*Primary Examiner*—Francis J. Jaworski

(57) ABSTRACT

An ultrasound transducer assembly is disclosed having a housing, a transducer array mounted in the housing and an electronics assembly mounted in the housing, the electronics assembly including one or more sub-assemblies having heat generating components disposed thereon. The electronics sub-assemblies further include thermal conducting features which conduct heat generated by the heat generating components out of the electronics assembly where it can be further removed by other thermal management techniques. These other thermal management techniques may include techniques utilized to cool the transducer array.

31 Claims, 11 Drawing Sheets

U.S. PATENT DOCUMENTS

| | | | |
|---|---|---|---|
| 5,882,310 A | 3/1999 | Marian, Jr. | 600/459 |
| 5,961,465 A | 10/1999 | Kelly, Jr. et al. | 600/459 |
| 6,050,943 A | 4/2000 | Slayton et al. | 600/439 |
| 6,142,947 A | 11/2000 | Tran et al. | 600/459 |
| 6,433,464 B2 | 8/2002 | Jones | 310/328 |
| 6,443,900 B2 * | 9/2002 | Adachi et al. | 600/458 |
| 6,445,580 B1 * | 9/2002 | Cohen et al. | 361/687 |
| 6,542,846 B1 | 4/2003 | Miller et al. | |
| 6,546,080 B1 * | 4/2003 | Geitz | 378/141 |
| 6,605,043 B1 | 8/2003 | Dreschel et al. | 600/459 |
| 6,645,145 B1 * | 11/2003 | Dreschel et al. | 600/443 |
| 6,669,638 B1 | 12/2003 | Miller et al. | 600/438 |

FOREIGN PATENT DOCUMENTS

| | | | | |
|---|---|---|---|---|
| JP | 41014211 | * | 4/1998 | 600/459 |
| JP | 200513461 | * | 1/2005 | 600/459 |

* cited by examiner

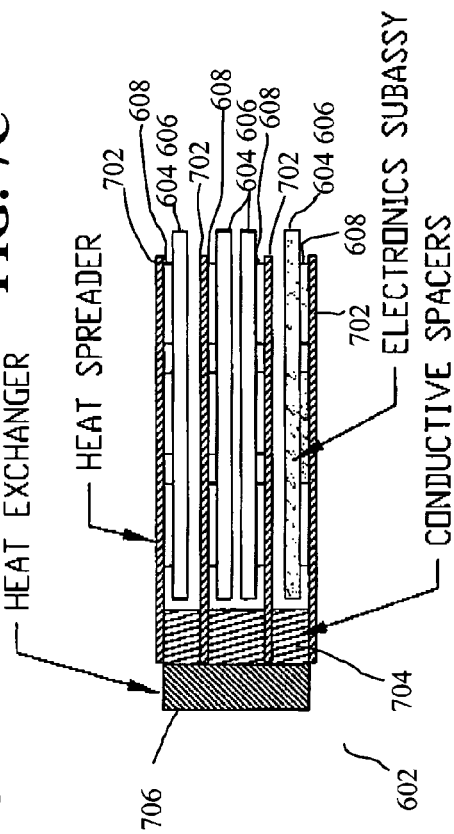
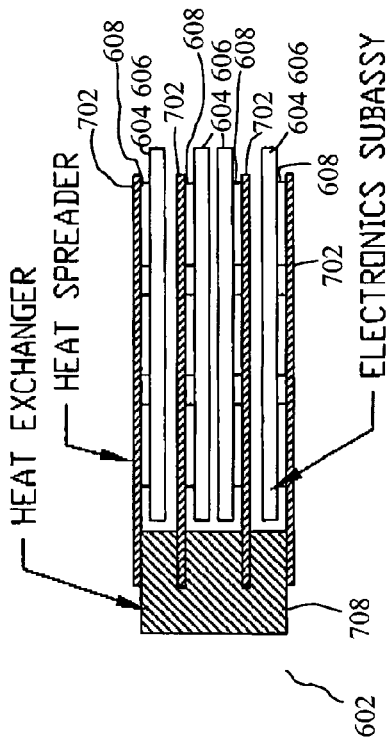
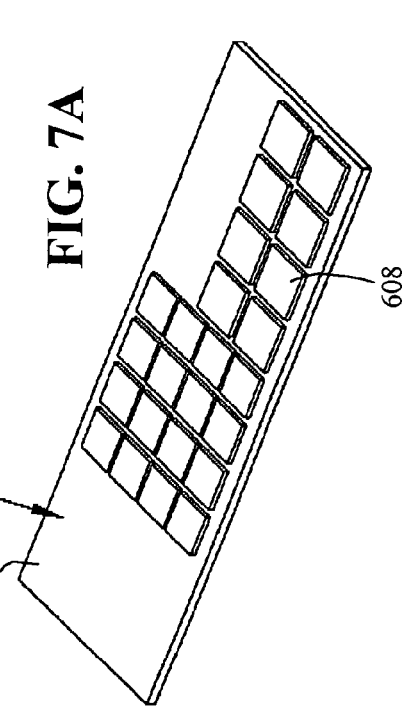
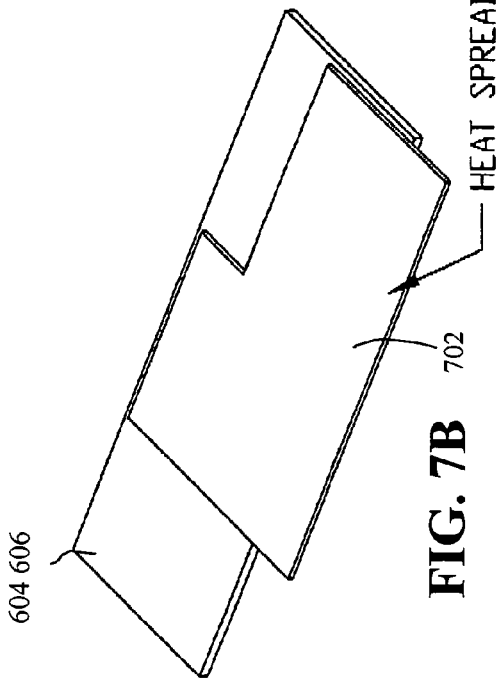

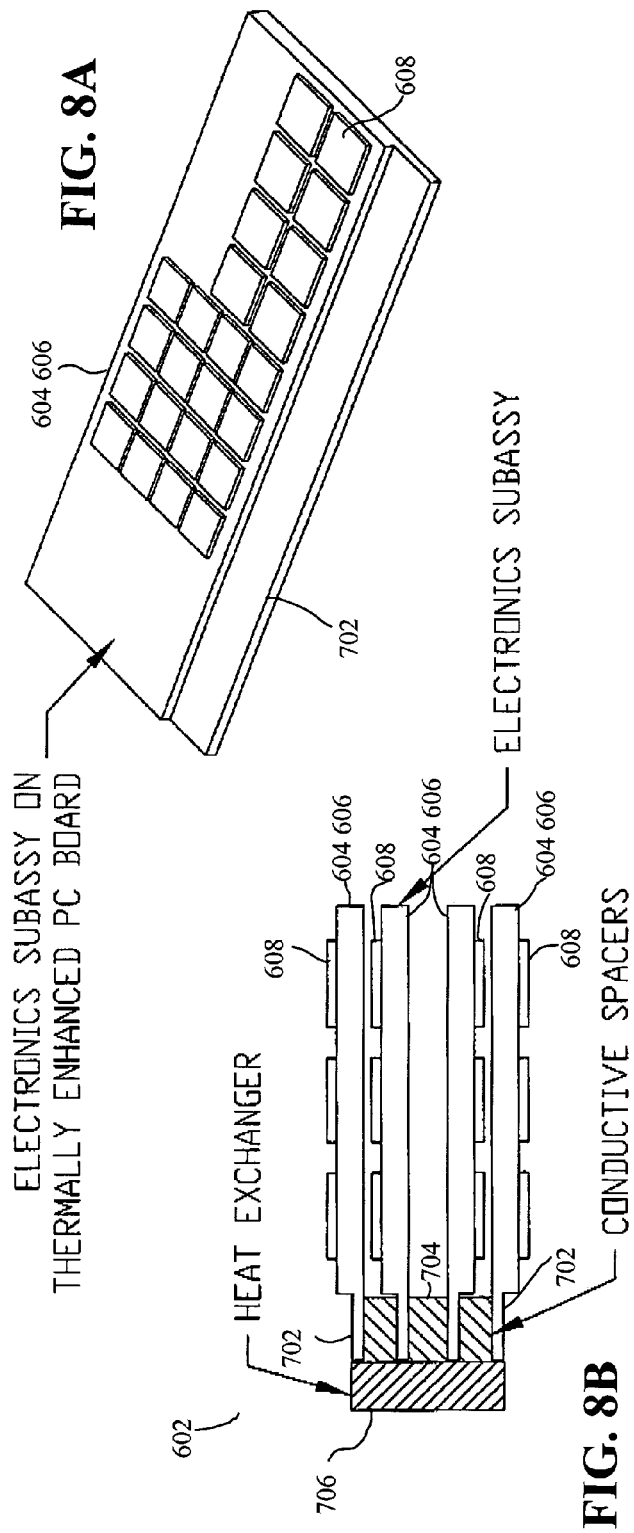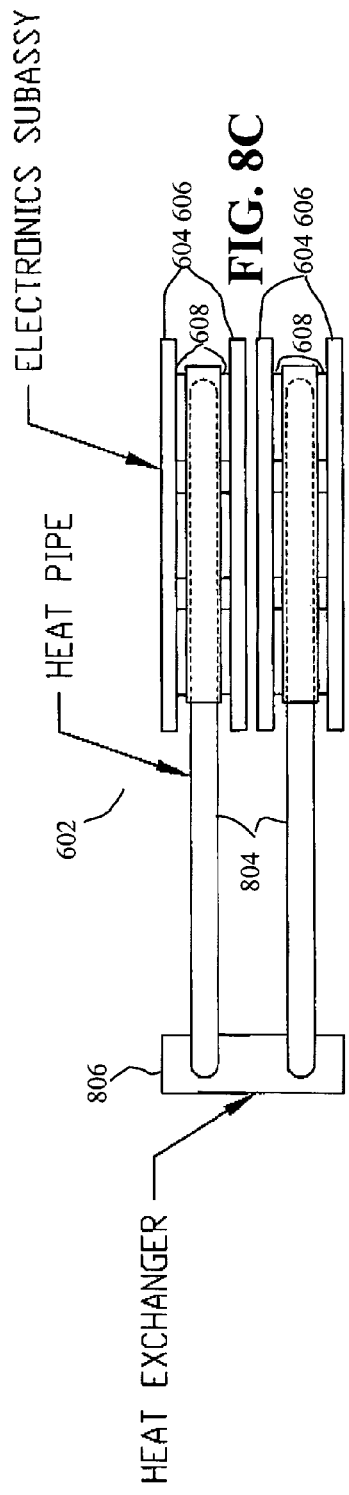

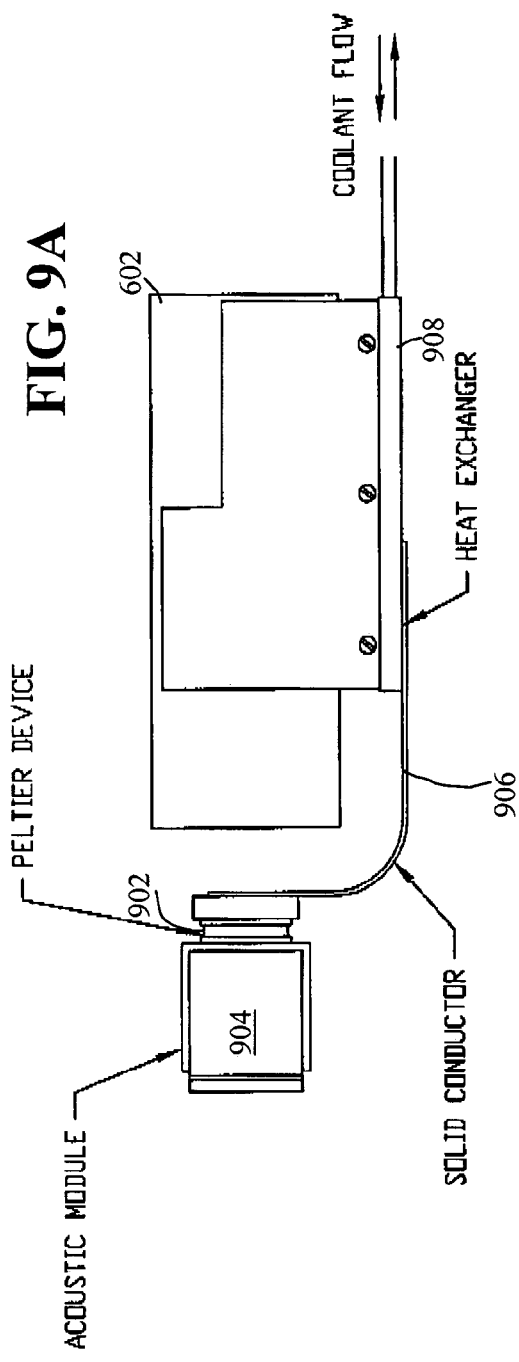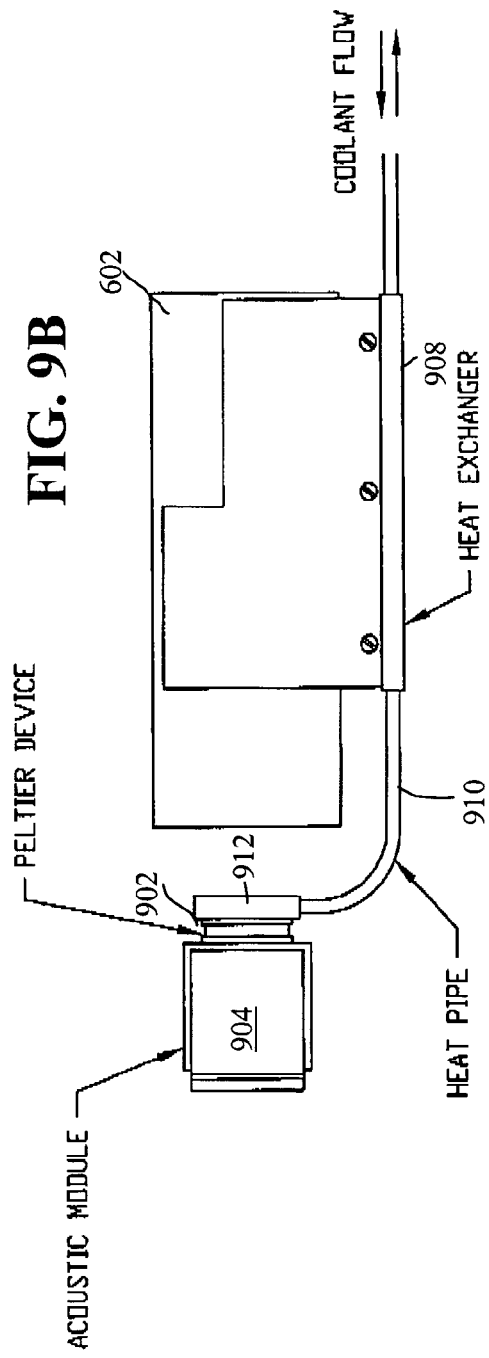

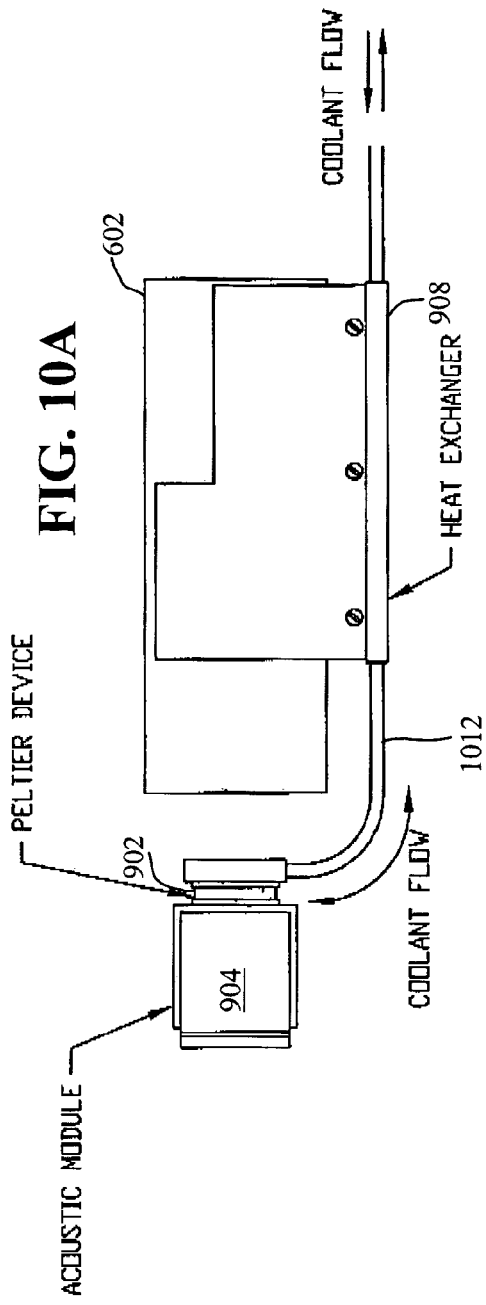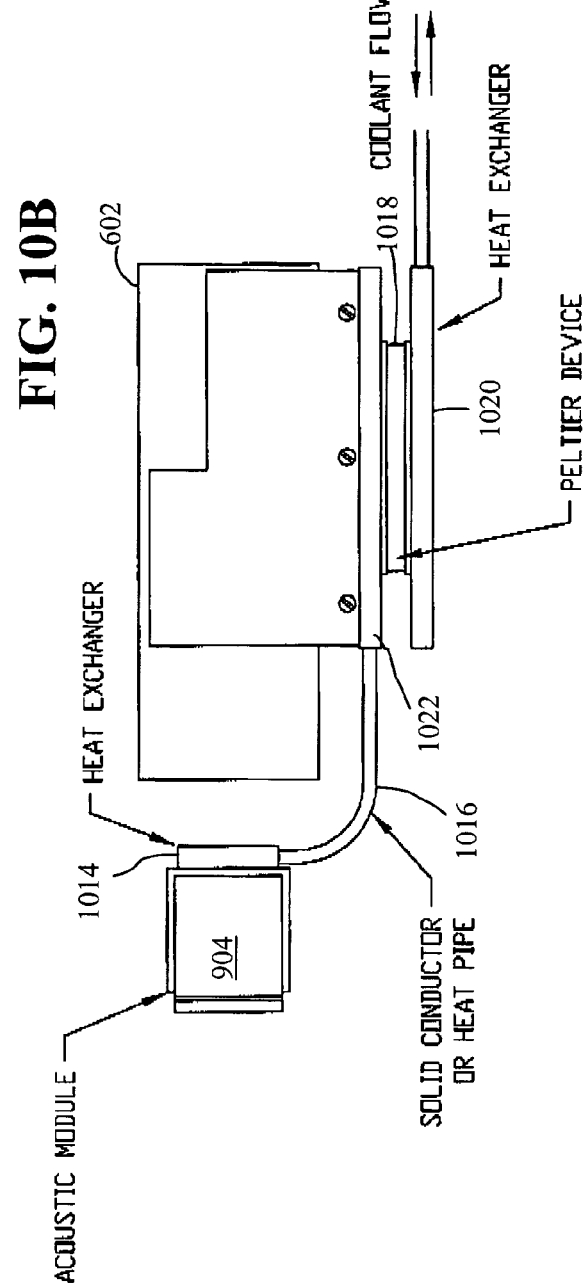

SYSTEM AND METHOD FOR ACTIVELY COOLING TRANSDUCER ASSEMBLY ELECTRONICS

REFERENCE TO RELATED APPLICATIONS

This application is a continuation-in-part under 37 C.F.R. § 1.53(b) of U.S. patent application Ser. No. 10/183,302 filed Jun. 27, 2002 (Ref. No. 2002P06482US (10791/30)) the entire disclosure of which is hereby incorporated by reference.

BACKGROUND

Medical ultrasound imaging has become a popular means for visualizing and medically diagnosing the condition and health of interior regions of the human body. With this technique an acoustic transducer probe, which is attached to an ultrasound system console via an interconnection cable, is held against the patient's tissue by the sonographer whereupon it emits and receives focused ultrasound waves in a scanning fashion. The scanned ultrasound waves, or ultrasound beams, allow the systematic creation of image slices of the patients internal tissues for display on the ultrasound console. The technique is quick, painless, fairly inexpensive and safe, even for such uses as fetal imaging.

In order to get the best performance from an ultrasound system and its associated transducers it is desirable that the transducers used to emit and receive ultrasonic pulses be capable of operating at the maximum acoustic intensity allowable by the U.S. Food and Drug Administration (FDA). This will help maximize the signal to noise ratio for the given system and transducer, help achieve the best possible acoustic penetration, and ensure that imaging performance is not limited by the inability to emit the full allowable acoustic intensity. Further, this will allow for maximum performance of the various imaging modes such as color flow, Natural Tissue Harmonic Imaging ("NTHI") and spectral Doppler. In NTHI mode, the transducer is excited at one frequency and receives the acoustic echoes at a second frequency, typically the second harmonic, in order to account for the non-linear propagation of acoustic waves through tissue and the harmonics created thereby. At the same time, there are practical and regulatory limits on the allowable surface temperature that the transducer may attain as it performs its imaging functions. For example, the Underwriters Laboratory (U.L.) Standard #UL544 "Standard for Safety: Medical and Dental Equipment" specifies an upper limit of 50° C. when measured in air and an upper limit of 43° C. when tested against a tissue mimicking material for the transducer portion contacting the patient's skin. It will be appreciated that there may be other regulatory standards or that these standards may be revised over time. In addition, sonographers prefer to grip a transducer case which is comfortably cool, thereby preventing excess perspiration in their hands and a potential to lose their grip on the device. Further, increased internal temperatures may affect the operational characteristics or capabilities of the transducer components, reducing their efficiency and/or operating capabilities. For example, CMOS integrated circuits, which may be utilized as part of the control circuitry in the transducer, operate faster and more efficiently at lower temperatures.

As the technology evolves, the use of more heat generating electronics within the transducer is commonplace. As described above, three constraints drive the need to maintain an operating temperature range for the electronics. The first constraint is the FDA imposed limit for patient contact. The second is the requirements of the customer/sonographer related to operator comfort and safety. The third requirement is the need to keep the temperature of the electronics at or below a maximum temperature for optimum performance. This combination of increased loads and temperature limits requires that new methods be developed to dissipate the heat generated by the electronics. In particular, some transducer designs may use an architecture which requires the assembly/packaging of many electronic subassemblies. These needs may be driven by both the physical design of the transducer handle housing as well as the type and number of components which must be located within it. For example, creating a handle with an optimal ergonomic grip may require a custom electronics package to fit the necessary components within the ergonomically shaped housing. These assemblies/packages, therefore, may have increased component densities and restricted access or result in oddly shaped electronics packages with component locations determined by the physical constraints of the transducer handle housing. As each subassembly may contain heat generating components that must be cooled, the resultant assembly of these modular electronic sub-assemblies will likely distribute heat sources within the entire volume of the electronics assembly and/or the resultant assembly may have a higher density of heat generating components in any one area depending on the overall packaging of the assembly. Additionally, the waste heat generated by the electronics increases the overall waste heat generated by the transducer and increases the burden on the various cooling systems implemented.

Additionally, the introduction of Chirp transmit waveforms, Multi-focus (dynamic transmit focus) and high frame rate imaging modes has significantly increased the requirements for transmit power of the transducer. This increase in operating power has necessarily led to an increase in operating temperatures.

Given that it is desirable to be able to operate at the maximum allowable acoustic intensity and also desirable to control the internal transducer operating temperatures as well as the surface temperature distribution of the patient and user-contacting portions of the transducer's surfaces, thermal engineering is a serious consideration during transducer design. There are essentially two possible paths to proceed on with regard to transducer thermal engineering.

The first path makes use of passive cooling mechanisms and involves insuring that the heat that is generated by the transducer electronics and both by the electroacoustic energy conversion process taking place in the transducer's piezoelements and by the acoustic energy passing through and/or into adjacent transducer materials is passively spread out to as large an external transducer surface area as possible. This heat spreading process is typically achieved internal to the transducer by thermal conduction through solid materials and subsequently from the transducer's external case employing natural free convection to the atmosphere and/or radiation to the environment. Ideally the external heat-convecting and/or radiating surface area would consist of the entire transducer's external surface area from which free convection and/or radiant cooling to the atmosphere can potentially take place in an unobstructed manner. Transducer manufacturers have thus incorporated various passively conducting heat-spreading plates and members inside the transducer's interior spaces to ensure the spreading of the heat to the entire transducer case surface. Such members work well, however, it is frequently the ability to get the heat out of the electronics and the electroacoustic elements themselves and into such adjacent internal thermal-sinking structures such as these commonly used spreading plates that provides a significant portion of the probes total thermal dissipation resistance. If this internal thermal path is not a good one it is difficult to spread the heat generated by the electronics and the piezoelements around the case. If the heat generated by the electronics and the piezoelements cannot be removed, and effectively coupled and sunk to the entire transducer case area, then the probe surface portion in contact with the patient runs hotter than desired as this probe portion is directly adjacent the piezoelements. Thus, even in the passive strategy, there is concern concerning three key mechanisms: a) removing the heat from the highly localized piezoelement or electronics regions; b) spreading said heat efficiently to the external case surfaces; and c) allowing for unobstructed natural convection and/or radiation from the warm transducer surfaces.

In any event, using this passive strategy, maximizing the external probe surface area onto which heat spreads in a fairly uniform manner minimizes the peak surface temperature attained anywhere on the probes surface during steady state convection/radiation of the probes heat to the ambient. This passive strategy amounts to spreading the heat load around to minimize the impact of the limited ability of free convection and/or radiation to dissipate heat. Its fundamental limitation is that, for most transducers, even if heat is spread uniformly on the external case surfaces, it only takes a few watts of transducer driving power to cause the average transducer surface temperature to become unacceptable either with respect to the patient or the sonographer. In these cases, and particularly for small transducers having small surface areas, one may find that one is unable to operate at the allowable acoustic intensity limit because of excessive temperatures.

FIG. 1 shows a prior-art medical ultrasound transducer 1 in schematic sectional view. Transducer 1 has a typically polymeric external case 2 which is gripped by the sonographer. The top of the transducer (+Y end) can be seen to have the typical acoustic lens 3 which serves to focus the ultrasound beam in the X-Y plane as it passes into the subject patient. Focusing in the Y-Z plane is done via electronic phase delays between the various piezoelements which are arranged on a Z-axis pitch and spacing passing into and out of the paper as is usual for phased array transducers. The bottom or back of the transducer 1 has emanating from it a flexible coaxial cable bundle 4. The cable 4 is shown in broken view at its midpoint to indicate its considerable length, usually on the order of 6 to 12 feet. Where cable 4 exits from the transducer 1, and specifically where it exits from the transducer case 2, can be seen a flexible strain relief 5. Strain reliefs are usually fabricated from a flexible rubber, such as silicone rubber, and they serve to prevent damage to the cable 4 or chemical leakage into the case 2 at the point of cable/case juncture particularly as cable 4 is flexed by the user.

A transducer cable connector 6 can be seen at the termination of the cable 4 (-Y end). The connector 6 is usually of a mass-actuated design and has an appropriate rotatable actuation knob 8 for that function. To the right of the transducer's connector 6 are shown in phantom a mating ultrasound system connector 7 mounted on an ultrasound system console 9. To use the transducer the sonographer would plug connector 6 into mating connector 7 (connectors shown unmated) thereby electrically connecting the transducer 1 to the ultrasound system console 9.

In the interior portion of the bottom of transducer 1, inside of polymeric case 2, portions of numerous electrical interconnects 10 (indicated by partial dotted lines) run from the transducer device 1 into the cable 4 and, in turn, into the connector 6. Generally a large number of interconnects 10 comprising coaxial wires of controlled impedance are provided in cable 4 to carry the electrical impulses transmitted to and received from the individual piezoelements making up the phased array. The details of how the interconnects 10 are mated to the piezoelements or to the connector are not shown as it is not critical to the understanding of this invention. It should be generally understood that numerous interconnects 10 pass from the transducer 1 and its piezoelements through the cable to the connector 6 and these serve an electrical function. Interconnects 10 must physically be routed through the interior of the back of the transducer case 2, and around whatever other means, thermal or otherwise, are located therein.

The electroacoustic transducer device assembly 50 is packaged and operated inside the confines of the polymeric case 2. Assembly 50 is shown schematically in FIG. 1 and in FIG. 2. Assembly 50 comprises acoustic backer material 11, a piezoelements 12 and one or more (one shown) acoustic matching layers 13. While the lens 3 is not shown in FIG. 2, it may also be considered part of the Assembly 50. Acoustic backer material 11 serves the functions of attenuating acoustic energy which is directed backwards to minimize reverberations and ringiness, and as a mechanical support for piezoelements 12. Materials used to fabricate backer 11 are generally poorly or only modestly thermally conductive as it is exceedingly difficult to design a highly thermally conductive yet acoustically highly lossy material. Piezoelements 12 may, for example, be fabricated from lead zirconate titanate (PZT) or composite PZT in a manner well-known to one of average skill. On top of piezoelements 12 is the matching layer or layers 13 which serve to act as an acoustic impedance transformer between the high acoustic impedance piezoelements 12 and the low acoustic impedance, human patient. (The human patient is not shown, but it should be understood that the patient is in contact with lens 3.)

The piezoelement material, typically PZT, is a ceramic having generally poor to modest thermal conductivity. The matching layer(s) 13 materials also frequently have poor to modest thermal conductivity because of their conflicting acoustic requirements. It is to be noted that the backer 11, the piezoelements 12 and the matching layer(s) 13 are all intimately bonded to each other and to the lens material 3 such that acoustic energy produced in piezoelements 12 may pass through the layer interfaces in the +Y-direction freely. Of course reflected acoustic echoes from the body may also likewise pass freely in the -Y direction, back into probe 1.

Not shown in FIG. 1 are horizontally running (+-X axis direction) electrodes in any of the interfaces of the type between lens 3 and layer 13, layer 13 and piezoelements 12 or piezoelements 12 and backer 11. Adequate thin electrodes must be present to apply and sense electrical potentials across the top and bottom surfaces of the piezoelements 12. Electrical interconnects 10 are typically routed and connected to such dedicated interface electrodes on a piezoelement by piezoelement basis (connections and routing not shown). The interface or surface electrodes are required to make electrical contact to each piezoelements 12 without appreciably negatively impacting the acoustic performance spectrum of transducer 1. Thus, such electrodes are typically chosen to be very thin, metallic, and have very little mass. This, in turn, causes the electrodes to be poor thermal conductors in the lateral X-direction.

Also shown in FIG. 1 are two symmetrically situated pairs of passive thermal conduction enhancement members 14 and 15 arranged on each side of assembly 50. Thermal member 14 is schematically shown physically and thermally connected to the edge region of element array 12 and layer 13, and possibly also to the ends of the interfacial or surface electrodes (not shown). Thermal member 15 is schematically shown thermally and physically connected to member 14. The members 14 and 15 are arranged to be in close juxtaposition and in good thermal contact with the interior walls of case 2. It will be noted that thermal member 15 may typically be thicker (as shown) and therefore more thermally conductive than member 14 given the increased space toward the cable end of the transducer. Further, member 15 may be composed of more than one component which, combined, perform the function of member 15. In one such representative example, items 14 would consist of thin films of flexible copper, perhaps in the form of a flexible circuit, extending away from the edges of the piezoelement array 12 and possibly emanating from within an interface such as the interface between backer 11 and array 12, array 12 and layer 13 or layer 13 and lens 3 wherein it also serves an aforementioned electrode function. In this example, the primary purpose of member (or flex circuit) 14 is electrical interconnection as necessary in the interfaces between at least certain of the laminated layers. Items 15 would typically consist of aluminum or copper plates, perhaps between 0.010–0.080 inches thick, which are bonded or thermally coupled intimately to the inner surfaces of case 2. The joint between members 14 and 15 must be thermally conductive. If member 14 is an electrical flex circuit used for interconnection, then care would be taken to provide only a thermal joint and not an electrical joint so as not to short out the flex traces which need to be routed (not shown) backwards to interconnects 10.

As the sonographer or user images with transducer probe 1, the system console 9 transmits a series of electrical pulses through the connectors 7,6 and cable 4 to the acoustic array of piezoelements 12. The electroacoustic piezoelements 12 convert the electrical pulses to acoustic output energy emanating from the rubber lens 3 into the patient. During the ultrasound reception portion of the acoustic beamforming, the piezoelement senses in a passive mode the electrical disturbance produced by acoustic energy bounced off of internal patient tissue and reflected back into the transducer 1. It is primarily the transmit portion of imaging when heat is produced by the piezoelements. This is because the electroacoustic energy conversion process is less than 100% efficient. Thus the piezoelements 12 act as unintended heaters. Secondly, as ultrasound energy is produced by the piezoelements 12, it is somewhat absorbed by layers 13 and lens 3, such layers usually not being totally lossless. The unavoidable nonzero portion of acoustic energy which is directed away from the patient into the backer 11 also serves to generate heat in backer 11. Thus, we have heat being directly generated in the piezoelements 12 and indirectly generated in backing material 11, matching layer(s) 13 and lens 3.

A thermal member 14, if comprised of a flexible circuit being formed in part of a thin metal such as copper, offers modest thermal conduction of heat generated by piezoelements 12 laterally in the X and Z directions to the edges of the device and then downward to some more significant thermal sink, such as 15. The purpose of member 15 is to render isothermal the inner surface of the case 2 so that heat may be encouraged to flow across the case wall at all locations. The thermal purpose of member 14 is to get the heat away from the piezoelements 12 and redirected so that it can be flowed into said isothermalization member 15.

Using the combination of thermal elements 14 and 15 it has been possible to passively spread the heat out isothermally to most of the interior case 2 surfaces. It should be understood that case 2, being fabricated of a polymer, will typically conduct heat poorly. It is therefore critical to get the heat spread out over most or all of the interior surface of case 2 so that although the thermal resistance across the thickness of the case wall 2 is high, there is considerable surface area to compensate for this fact and keep the overall thermal resistance between the elements and the environment as low as possible.

Heat which is generated in matching layer(s) 13 and lens 3 may also be conducted downward toward the piezoelements 12 or to their interfacial electrodes (not shown) which can, in turn, pass heat to the edges of the stack for redirection downward in the −Y direction via member 14 for example. When transducer probe 1 is in contact with a patient's tissue, some heat may pass directly into the patient. In any event, the U.L. limitation on skin or tissue temperature severely limits the temperature of the lens, and heat dissipation toward the patient.

Heat which is generated in backing material 11 may be passed to thermal means such as member 15. Member 15 may be arranged to actually envelope or wrap around backer material 11 in the form of a metallic thermal container or can (not shown) in order to facilitate the passage of heat from backing material 11 into thermal member 15 and out of transducer 1.

Thus, the ability of probe 1 to shed heat to the environment is governed primarily by passive free convection and/or radiation of heat from the probe's external surfaces. There is a rather limited capacity to remove heat by radiation to the environment and/or natural convection of air past the external probe surface even in this optimal isothermalized example. In practice, given the limits on the temperature of lens 3 and sonographer gripping comfort, it is not possible to dissipate more than a few watts of thermal energy in this passive prior-art manner. Also, different sonographers typically cover different amounts of the probe surface with their hands as they grip it, and in some cases much of the heat is being transmitted by conduction directly into the sonographer's hand(s). This can produce sonographer discomfort and a poor grip. If the only heat dissipating surface and path available is the external case surface dissipating by convection and/or radiation to the atmosphere or by conduction into the patient and/or the sonographer's hand, then severe power dissipation limits of a few watts will apply, particularly to small probes having small surface areas even if that surface area is isothermalized.

Others have attempted to increase the lateral (X-axis) and/or vertical (Y-axis) thermal conductivity of acoustic backing material 11, piezoelements 12 and acoustic matching layers 13. Although these measures may help keep the face of the acoustic array more isothermal particularly for very large array probes, they do nothing to increase the capacity to remove heat from the probe's external surfaces in an improved manner.

An extension of the passive-cooling approach has included an attempt to conduct or spread some of the heat down the length of the attached cable in order to permit the cable to offer more passive convection and/or radiant surface area. This helps the situation only incrementally because of the user-preferred small diameter cable and the difficulty of providing much of a thermally conductive path in such a small diameter cable without compromising the desired flexibility and compactness of the cable. Such an incremental measure is described in U.S. Pat. No. 5,213,103 "Apparatus for and method of cooling ultrasonic medical transducers by conductive heat transfer" by Martin, et al.

As a specific example a copper braid could be routed from the case 2 interior into at least some limited length of the cable 4 adjacent to device 1. This copper braided thermal means may be connected to a thermal means in the case such as depicted member 14, 15 or 14 and 15 or may also serve as item 15 for example. This tact essentially creates additional dissipative surface area on the cable.

It should be noted that for endocavity transducers (probes inserted internally into the human body) heat is dissipated both by direct conduction to the patient's internal tissues and fluids, as well as by the conduction out the cable and convection and/or radiation from the exposed transducer handle which remains external to the patient's cavity. We must also control the maximum surface temperatures attained by these probes.

The second strategy for cooling transducers is to utilize active cooling rather than passive cooling in order to dissipate heat well beyond that which can be passively convected and/or radiated or conducted from the external transducer surfaces. Active cooling means that one provides a means to actively remove heat from the transducer such as by employing a pumped coolant or other active refrigeration means. Using active cooling one may ensure that one is always able to operate the acoustic transducer up to the allowable acoustic intensity limit while also maintaining acceptable surface temperatures regardless of how small the transducer is or how much surface area it offers for cooling relative to its acoustic intensity.

At least part of the reason active cooling has not yet been used is because of the apparent cost, reliability and the ease-of-use issues associated with it. There is a well-established continued trend in the ultrasound industry toward reliable "solid-state" phased array transducers with no moving parts and with excellent chemical resistance to disinfection procedures, including procedures involving total chemical immersion for extended periods. There is a more recent trend toward minimizing the cost of ownership for all medical implements as well as any need to service or repair them. Both of these trends place very severe constraints on any potential active transducer cooling means for use in the hospital, clinic or doctor's office environment.

Finally, one must keep in mind that imaging transducers are plugged into and unplugged from the ultrasound console's various connector ports in a varying personalized manner, thus any active cooling scheme should preferably continue to allow for the freedom to do this and should not substantially complicate the integrity or ease of this connection. Large numbers of connector plug/unplug cycles should also not degrade the performance of the active cooling means. Any active cooling scheme should involve minimal additional maintenance and should be as transparent to the user as possible.

BRIEF DESCRIPTION OF THE DRAWINGS

FIGS. 7A–7D show exemplary electronics subassemblies and electronics assemblies using heat conductive sheets for use with the embodiment of FIG. 6.

FIGS. 8A–8C show exemplary electronics subassemblies and electronics assemblies using heat conductive printed circuit boards or heat pipes for use with the embodiment of FIG. 6.

FIGS. 9A–9B depict exemplary methods of coupling the cooling system of the transducer module with the cooling system of the electronics assembly for use with the embodiment of FIG. 6.

FIGS. 10A–10B show alternate exemplary methods of coupling the cooling system of the transducer module with the cooling system of the electronics assembly for use with the embodiment of FIG. 6.

DETAILED DESCRIPTION OF THE PRESENTLY PREFERRED EMBODIMENTS

The invention relates to imaging of materials in living tissue, and in particular to increasing the power output of transducing means used for acoustic imaging by compensating for thermal problems associated with such increased power output using active cooling. For more information about using active cooling in transducers, refer to U.S. Pat. No. 5,560,362, herein incorporated by reference.

As described above, current transducer designs incorporate a flexible circuit board connection to one side of the piezoelectric material for signal connection, and a copper foil acting as the ground electrode at the other side of the piezoelectric material. It will be appreciated that other types of transducers may require different grounding structure. For example, a 2-D array type transducer may require a flex-circuit to provide individual ground electrodes for each element. Some of the heat generated by the PZT and the first impedance matching layer can be taken away form the face of the probe using these layers. The current transducer designs thermally connect these copper layers to the thermal dissipation plates at the transducer handle, which results in improved thermal performance.

Figure 3:
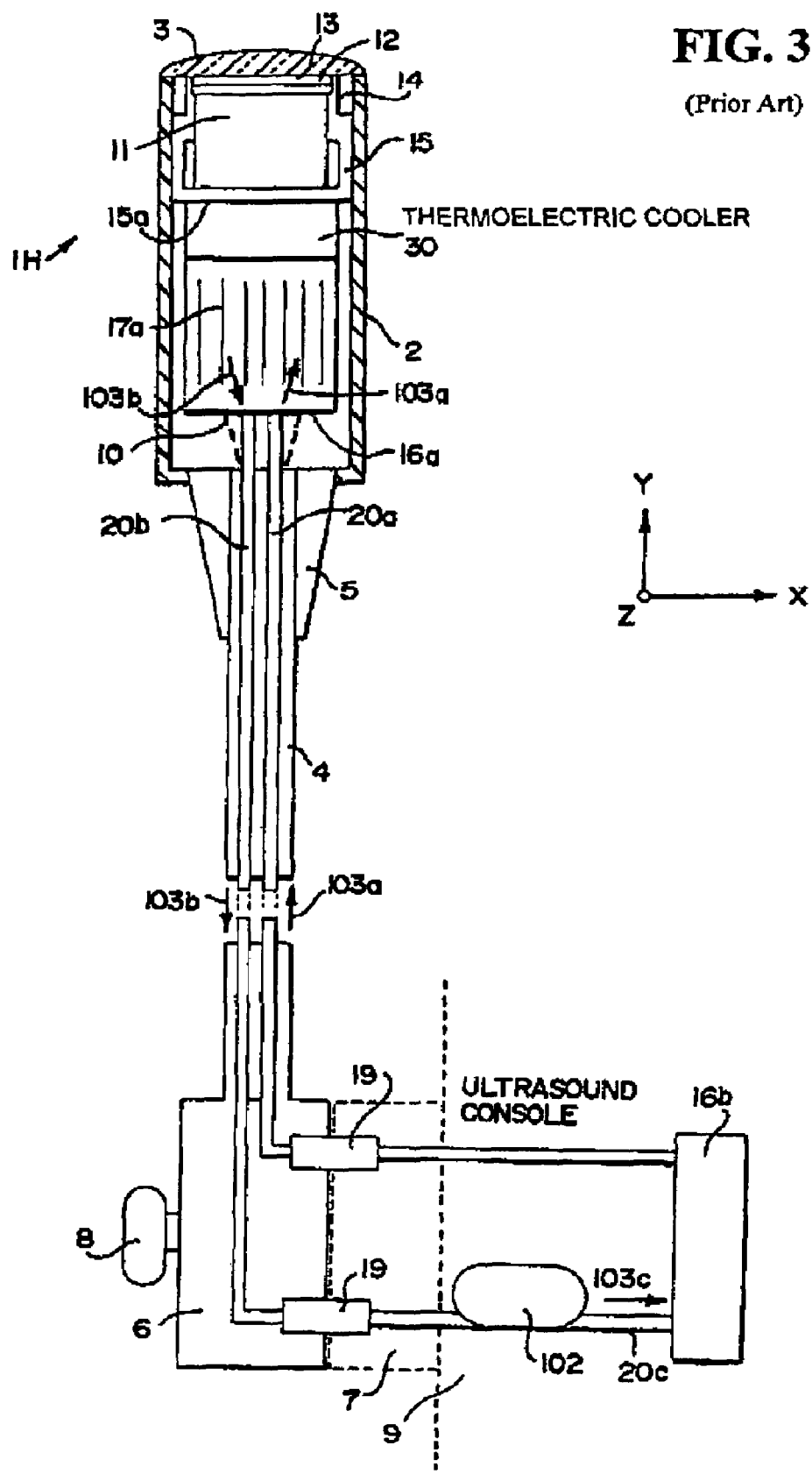
FIG. 3 is a partial cross-sectional view of a transducer assembly wherein a thermoelectric cooling device is thermally coupled to the heat dissipating piezoelements and their local associated passive heat dissipating members.

FIG. 3 depicts a system which uses a thermoelectric cooling device 30, such as a Peltier device, in the thermal path between passive conducting members 15, 15A and heat exchanger 16A. Note that the thermal member 15A extends beneath acoustic backer 11 such that heat may be deposited in the top cooling surface (+Y surface) of thermoelectric cooler 30. Cooler 30 would typically consist of an electrically powered junction device capable of establishing a thermal gradient and transporting heat through its thickness along the Y axis (sometimes referred to as a Peltier device). Such devices, although capable of moving appreciable quantities of heat, are typically rather inefficient. Thus, the cooling system components described in U.S. Pat. No. 5,560,362 may be used to carry away not only the piezo-element heat pumped by cooler 30, but also the waste heat generated by the cooler 30 itself. Specifically, such thermo-electric coolers 30 are available, for example, from Marlow Industries, Inc. (10451 Vista Park Road, Dallas, Tex. 75238) with heat removal capacities covering the range from 1 to 150 watts. The cold (cooling) side of cooler 30 may, depending on the heat load and specific type of cooler, have the capacity to subcool between 10 and 100 degrees centigrade. Use of a thermoelectric cooler 30 offers advantages of dynamic realtime temperature control of the transducer piezoelements and/or the thermal capacity to actually subcool the piezoelements 12 as described without requiring a conventional freon-style refrigeration system. The reader will realize that the thermoelectric cooler 30 may be arranged to dump its heat to any of the other known thermal dissipation means.

A specific advantage of a thermoelectric cooler 30 is appreciated when performing high frequency ultrasound imaging of near-surface tissues. In these growing applications, increasing amounts of heat energy are being generated in the probe and in the tissue as manufacturers attempt to achieve the highest possible resolution at the maximum allowable acoustic intensities. It would be rather difficult to maintain a reasonable lens temperature unless a cooling device 30 having very large cooling capacity (a device capable of subcooling may serve this purpose) is present in close proximity to the piezoelements, lens and tissue.

As opposed to coupling the thermo-electric cooler with the passive conducting members 15, 15A as described above, one can improve the heat transfer between the copper foils and the thermal plates by placing the thermo-electric cooling device in between, such that the hot junction of the thermo-electric cooling device is in contact with the thermal plates and the cold junction is in contact with the copper foil. Herein, the phrase "coupled with" is defined to mean directly connected to or indirectly connected through one or more intermediate components. This helps to maintain the temperature of the copper foil at a lower temperature while increasing the temperature of the thermal plates. The thermal plates are in contact with the plastic parts at the transducer handle. If the transducer handle is made of thermally conductive materials, the overall thermal dissipation of the device may be improved. Alternatively, the thermal plates or the hot junction of the thermo-electric cooling device can be connected to the overall transducer cable jacket. The overall transducer cable shield has a large surface area. The surface area of the conductors in the cable jacket shield is 200 cm×1 cm. This is much larger than the surface area of the transducer (1.9 cm×1.4 cm) or the handle (about 80 cm$^2$).

Figure 4:
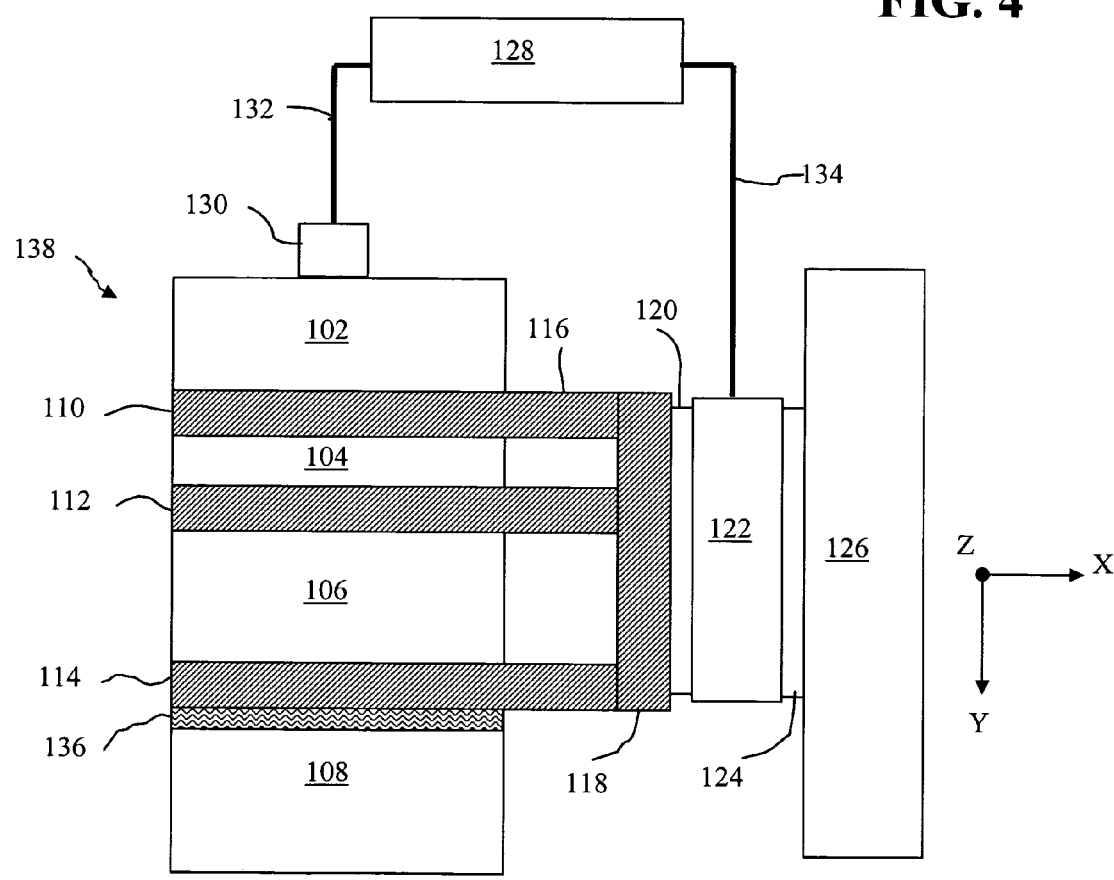
FIG. 4 depicts a block diagram of a transducer assembly according to one embodiment.

FIG. 4 shows a block diagram of a transducer assembly 138 according to a first embodiment. The assembly 138 includes a backing layer 102, a piezo-electric layer 104, impedance matching layer 106, and a mechanical lens 108. The piezo-electric layer 104 is preferably a PZT layer 104, as described above, and the mechanical lens 108 is preferably made of silicone rubber, although one of ordinary skill in the art will recognize that other materials may be used. Further, one of ordinary skill in the art will appreciate that other mechanisms for generating ultrasonic energy may also be used as will be discussed below.

In the first embodiment, flex circuit layers 110, 112 including flexible signal connections and electrical ground connections, are sandwiched between the transducer layers 102, 104, 106. It will be appreciated that the transducer assembly may have more or fewer functional and electrical connectivity layers and that other materials may be used in place of or in addition to the disclosed materials. The Flex circuit layers 110, 112 preferably comprise a material that is thermally conductive in addition to being electrically conductive, such as copper. A thermo-electric cooler 122, and specifically, the cold junction of the thermo-electric cooler 122, is thermally coupled 116, 118, 120 with the flex circuit layers 110, 112. The thermal coupling is preferably implemented so as not to interfere with the electrical operation of the flex circuit layers 110, 112 and operation of the transducer 138. The thermo-electric cooler 122, and specifically, the hot junction of the thermo-electric cooler 122, is thermally coupled with a heat sinking device 126. The heat sinking device 126 may be an active or passive cooling system as described above, the transducer case, or a phase-change material based heat dissipation system, as described below. The heat sinking device 126 removes heat dissipated by the thermo-electric cooler 122 from the transducer 138 as well as heat generated by operation of the thermo-electric cooler 122 itself.

In operation of the transducer 138, heat is generated within the various layers 102, 104, 106, 108 as described above. The generated heat is convected away from the layers 102, 104, 106, 108 by the heat conductive flex circuit layers 110, 112 and out of the transducer along the thermal path 116, 118, 120 to the thermo-electric cooler 122. An electrical current passing through the thermo-electric cooler (electrical connections not shown) causes the thermo-electric cooler 122 to convect heat from its cold junction to its hot junction, as described above and as is known in the art. The generated heat is then passed to the heat sinking device 126. By coupling the thermo-electric cooler 122 directly to the flex-circuit layers 110, 112, the heat generated within the layers 102, 104, 106, 108 of the transducer 138 is more effectively dissipated. As noted above, it is frequently the ability to get the heat out of the electroacoustic elements themselves and into adjacent internal thermal-sinking structures that provides a significant portion of the probes total thermal dissipation resistance. Given that the flex circuit layers 110, 112 are typically poor thermal conductors, as described above, this placement of the thermo-electric cooler 122 substantially proximate to the transducer assembly 138 and in direct thermal contact with the flex circuit layers 110, 112 without the need for intermediary passive thermal members, results in more effective and efficient heat dissipation.

In a second embodiment, the heat generated during operation of the transducer 138 can also be taken away from the other layers 102, 104, 106, 108 of the transducer assembly 138 such as the mechanical lens/window 108 or the impedance matching layers 106. To accomplish this, b a thin (<0.1 λ, λ being the wavelength in the layer material) layer of thermally conductive material, such as copper or a metal mesh, may be embedded in the RTV lens 108 and/or impedance matching layers 106 and similarly coupled with the thermo-electric cooler 122.

As was noted, the cooling capacity of the thermo-electric device 122 can be controlled via the input electrical current to the device 122. In a third embodiment, a feed back control circuit 128 is provided to monitor the temperature of the probe and adjust the electrical current supplied to the thermo-electric cooling device 122 in order to maintain the optimum condition under all operating environments. The feed back control circuit 128 is coupled 134 with the current supply control of the thermo-electric cooler 122 and with a temperature sensor 130 which allows the circuit 128 to monitor the probe temperature. The feed back control circuit 128 may be controlled by the user or controlled automatically to maintain desired probe operating temperatures, indicate or prevent thermal overloads, or otherwise maintain optimal probe operation. Further, the feed-back control circuit 128 may be used to efficiently operate the thermo-electric cooler 122 only when necessary to achieve a desired probe temperature thereby avoiding unnecessary operation of the cooler 122.

In a fourth embodiment, the heat sinking device 126 includes a phase change material such as wax in the case or case walls of the transducer housing (not shown) to dissipate the heat generated by the thermo-electric cooling device 122 itself. The polarity of the voltage supplied to the cooler 122 may be reversed when the transducer 138 is not generating heat or in not operating in a thermally limited mode to cool down the phase change material. This may be controlled by the feed back control circuit 128.

In a fifth embodiment, separate thermo-electric coolers 122 may be provided to dissipate the heat generated by one or more of the layers 102, 104, 106, 108, as described above.

It will also immediately be recognized by those skilled in the art that one may easily use the thermo-electric cooler 122 to also heat the probe such that it is warm and comfortable to the patient's touch when first used. Alternatively one might ensure that the probe operates at all times at a desired temperature setpoint (including when the probe is first switched on) or below such a setpoint or above a lower setpoint and below a second higher setpoint. This can be achieved by reversing the polarity of the current supplied to the thermo-electric cooler 122 as described above. The cooler 122 might also be used to cool the probe to prevent damaging it during hot disinfection or sterilization procedures used to clean the probe.

Figure 5A:
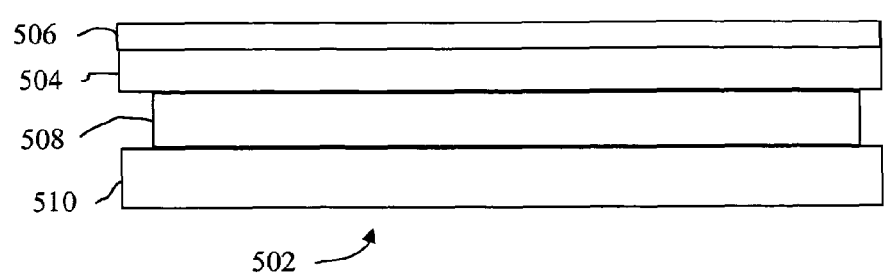
FIG. 5A shows a micro-mechanical based ultrasound transducer assembly according to an alternate embodiment.
Figure 5B:
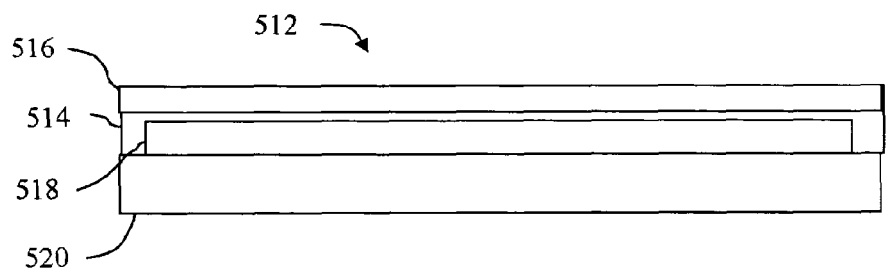
FIG. 5B shows a micro-mechanical based ultrasound transducer assembly according to another alternate embodiment.

FIGS. 5A and 5B show cross sectional views of a sixth embodiment using micro-mechanical based ultrasound transducers such as capacitive micro-mechanical ultrasound transducers ("cMUT's"). Such transducers use micro-mechanical components fabricated using integrated circuit fabrication techniques to generate the ultrasonic energy and receive the resultant echoes for diagnostic imaging. For more information about cMUT's and other micro-mechanical based ultrasound transducers, refer to U.S. Pat. No. 6,605,043 "DIAGNOSTIC MEDICAL ULTRASOUND SYSTEMS AND TRANSDUCERS UTILIZING MICRO-MECHANICAL COMPONENTS", herein incorporated by reference.

FIG. 5A shows a micro-mechanical based ultrasound transducer assembly 502 having a thermo-electric cooling device 508, as described above, attached thereto. The micro-mechanical transducer elements 506 are fabricated on a substrate 504, such as a silicon wafer, although other substrate materials may be used. The cold junction of the thermo-electric cooling device 508 is thermally coupled, such as by a thermally conductive glue, with the back of the substrate 504 so as to conduct heat generated by the micro-mechanical transducer elements 506 away from the substrate. A heat sinking device 510, such as the heat sinking devices described above, is coupled with the hot junction of the thermo-electric cooling device 508 to dissipate the heat generated therefrom.

FIG. 5B shows a transducer assembly 512 according to an alternate embodiment. The transducer assembly 512 includes micro-mechanical transducer elements 516 fabricated on a substrate 514, such as a silicon wafer. A thermo-electric cooler 518 is fabricated on the opposite side of the substrate material 514 such that the cold junction of the thermo-electric cooler 518 is proximate to the micro-mechanical transducer elements 516. A heat sinking device 520, such as the heat sinking devices described above, is coupled with the hot junction of the thermo-electric cooling device 518 to dissipate the heat generated therefrom. Alternatively, the thermo-electric cooler 518 can be integrated/fabricated on the same side of the substrate 514 as the micro-mechanical ultrasound elements 516, for example, off to one side.

It will be appreciated that the embodiments utilizing micro-mechanical ultrasound elements may use the feedback control circuit described above. Further, the heat sinking devices 510, 520 may be active or passive devices, as described above, and appropriately designed to channel the dissipated heat to a desired point within or outside the transducer housing.

In addition to the transducer assembly, modern transducer designs often incorporate either active or passive heat generating electronics assemblies, also referred to as electronics packages, within the handle of the transducer. As also used herein, the electronics "package" may also refer to the entire collection of electrical components included within the transducer handle housing, as both electrically and physically assembled and arranged. These electronics assemblies include discrete components, such as resistors, switches, integrated circuits, etc. and/or printed circuit boards ("PCB") having such discrete components affixed thereto on either one or both sides and/or the one or more edges of the PCB. The various discrete components are typically affixed to one or more PCBs, referred to as electronics sub-assemblies. These sub-assemblies are then assembled to form one or more electronics assemblies, such as by stacking, plugging, soldering, wiring or otherwise interconnecting the sub-assemblies, both physically and electrically, such as by connecting each sub-assembly with a common back-plane PCB or with a common electrical/signal bus. While the number of discrete components is largely driven by technical and functional requirements and limitations, the configuration and number of sub-assemblies and assemblies is driven by both the required functionality and also the physical design of the transducer handle into which the components have to fit. When assembled into an electronics assembly, the various discrete components of the sub-assemblies may be oriented on a surface that is external to the overall assembly or may be located or concealed within, i.e. internal to, the assembly. Discrete components of one or more sub-assemblies located in the interior of, i.e. concealed or partially obscured within, an assembly may be in close proximity to one another, with little or no space between them. One family of potential heat sources are integrated circuits (IC's) that transmit signals to the ultrasound transducer assembly and receive signals from the ultrasound transducer assembly. These IC's may be located in many different places, i.e. on different assemblies within the transducer handle or may be concentrated within an assembly of sub-assemblies. In the simplest case for heat transfer, they may be on the surface of an electronics assembly, i.e. on the external outwardly facing surface. The mechanical/physical requirement for a compact, space efficient assembly strains the ability to keep that assembly within the optimal operating temperature due to the difficulty with removing heat from the assembly. In one embodiment, heat generating components may also be located on the back side of the cMUT transducer substrate, as described above and shown in FIGS. 5A and 5B. For the purposes of the disclosed embodiments, this substrate having heat generating components on one side and micro-mechanical transducer elements on the other side, may be considered a circuit board and part of an electronics sub-assembly or assembly, as described. Further, cooling methods described above for micro-mechanical arrays may be used to further cool the components also located on the substrate. Alternatively, or in addition to these cooling methods, the methods described below may be used to both remove heat from the substrate-mounted components and the micro-mechanical transducer array itself.

The electronics package, of which a given transducer may have more than one, is the collection of electronics assemblies, and their subassemblies, as physically packaged for incorporation into the transducer handle during manufacturing. There may be transducer manufacturing assembly techniques that distribute the heat generating components within the volume of the electronics package in a modular fashion. However, when several electronic subassemblies are assembled together, such as stacked, in an assembly, methods that allow the heat to be pulled from within the electronics assembly are necessary. In embodiments using micro-mechanical based transducer arrays, multiple subassemblies or assemblies may be placed in close proximity to the transducer substrate and the components located thereon.

For components located on the outer surface of a particular assembly or components that are physically accessible, direct contact may be used to remove thermal energy. In one embodiment, a thermoelectric device, such as a Peltier cooling device described above, may be placed with the cool of the device in direct contact with the component to be cooled. The hot side of the thermoelectric device may then be coupled with either an active or passive device to further remove the thermal energy from the thermoelectric device.

Figure 6:
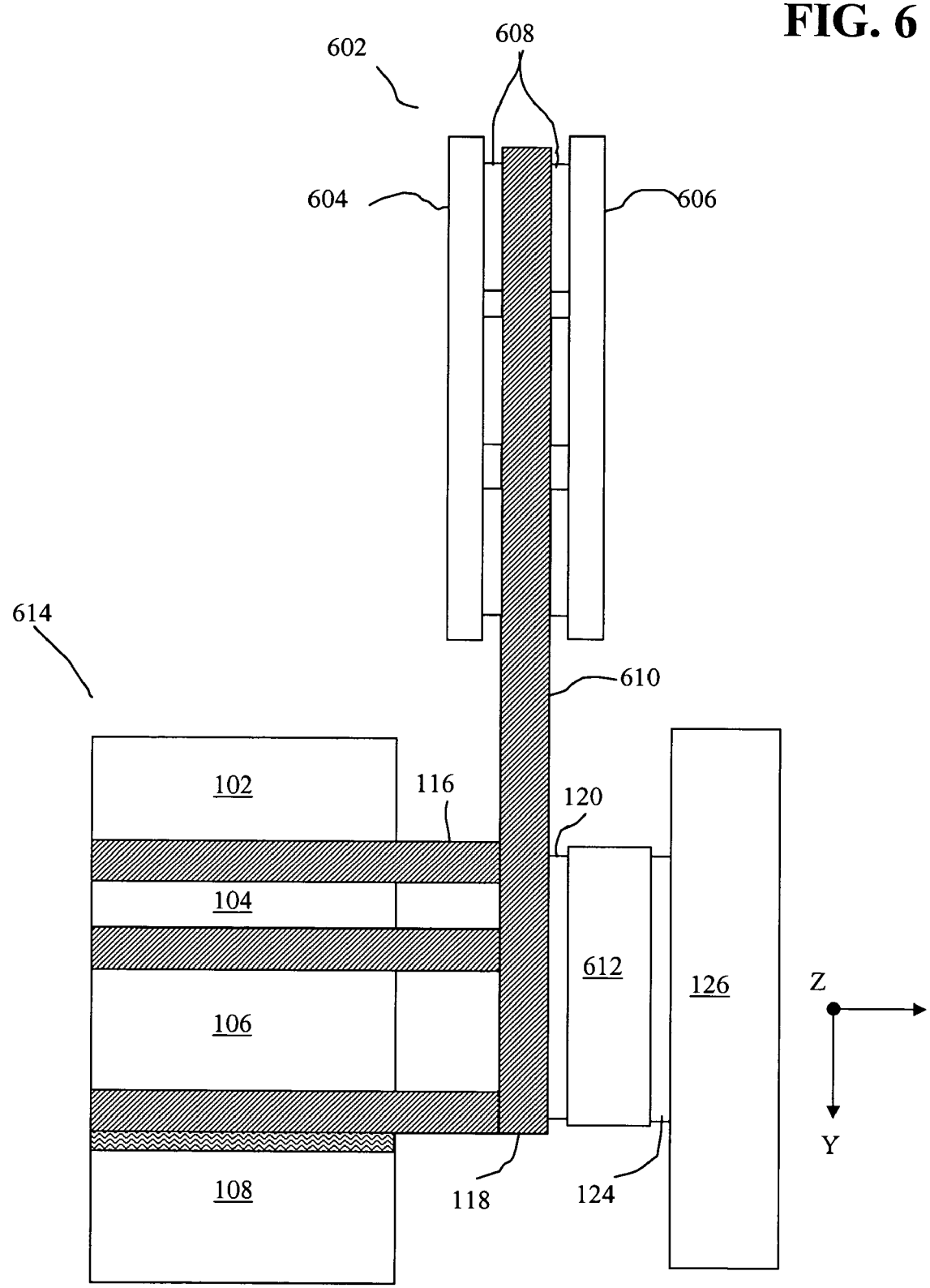
FIG. 6 shows an alternate embodiment of the transducer assembly of FIG. 4 wherein the thermoelectric cooling device is further coupled with the transducer probe electronics assembly.

FIG. 6 shows one method of cooling an electronics assembly 602 by sharing the thermoelectric cooling system described above. The assembly 602 includes one or more sub-assemblies 604 606 on which discrete components 608 are affixed. A thermally conductive mechanism 610, described in more detail below, is placed between the sub-assemblies 604 606 so as to conduct thermal energy from inside the assembly 602 to the outside of the assembly 602 and further to the cold side of the thermoelectric device 612 which then removes the thermal energy, in addition to the thermal energy from the transducer piezoelectric module 614, as described above.

One method of cooling an electronics assembly 602, which consists of several subassemblies 604 606 as described above and shown in FIG. 7A, is the use of sheets of sufficiently thick highly conductive material 702, such as copper as shown in FIG. 7B, as the thermally conductive mechanism 610 for pulling out the thermal energy from inside the assembly 602, as described above. The conductive sheets 702 may be fixed to the electronic subassembly 604 606 prior to the assembly of the electronics assembly 602 with a conductive epoxy. Additionally, the conductive sheets 702 may be thermally attached to the electronic subassembly 604 606 with conductive greases, pads or phase change interfaces that may or may not be required to be held in place with a separate mechanical clamp (not shown). During assembly of the electronics assembly 602, the conductive sheets 702 may be tied together with conductive connectors 704, such as conductive spacers 704 or other thermally conductive components, using fasteners or a conductive adhesive. This subassembly 604 606 may then be thermally attached to a heat exchanger 706 that transports the heat away through the use of a coolant flowing through the heat exchanger as shown in FIG. 7C. Other methods may also be implemented wherein the copper sheets 702 are directly attached to the heat exchanger 708, superseding the need for conductive connectors 704, as shown in FIG. 7D.

As shown in FIG. 8A, a second method of cooling an electronics assembly 602 which consists of several subassemblies 604 606 is to incorporate the functionality of the conductive sheet 702, described above, into the printed circuit board ("PCB") 802 on which the heat generating components 608 are mounted. This may be achieved through the addition of extra copper planes (not shown) within the PCB 802 or more efficiently by methods utilized in the ThermalClad® process by the Bergquist company, located in Chanhassen, Minn., in which the PCB is built on a thermally conductive substrate, usually aluminum or copper. In a method similar to the copper sheet 702 process discussed above, the conductive planes of the PCB 802 would be thermally connected to the heat exchanger 706 or 708, either via thermally conductive connectors 704, such as thermally conductive spacers or other thermally conductive components, as shown in FIG. 8B, or directly, similar to that shown in FIG. 7D. Alternatively, a suitable conductive material may be applied to the surface of the PCB, the material having openings, die cut, etched or otherwise, so as to be in contact with the surface of the PCB without interfering with the mounting or operation of the components affixed thereto. The conductive material may be a conductive sheet adhesively applied to the PCB. The conductive material is then further coupled with the heat exchanger as described above.

Another method of pulling heat out from within the modular electronics assembly 602 is the implementation of heat pipes 804, as shown in FIG. 8C. The heat generating components 608 may be thermally attached to small heat sinks in which a heat pipe 804 is mounted. The heat pipe 804 may efficiently move the heat from the hot component to a cooler heat exchanger 806 that is actively or passively cooled. Heat pipes 804 utilize a thermally conductive material (not shown) contained within the heat pipe 804 which changes its characteristics, such as its density or physical form (such as liquid to vapor), when it absorbs thermal energy. These changes cause the thermally conductive materials to move away from the heat generating components 608 and towards the cooler heat exchanger 806 where the changes are reversed by the removal of the thermal energy by the heat exchanger, thereby inducing a circulating/cyclical flow in the thermally conductive material which conducts thermal energy out of the assembly 602. Exemplary heat pipes which may be used with the disclosed embodiments include heat pipes manufactured by Thermacore, Inc., located in Lancaster, Pa. or Aavid Theralloy, LLC, located in Concord, N.H.

Figure 12A:
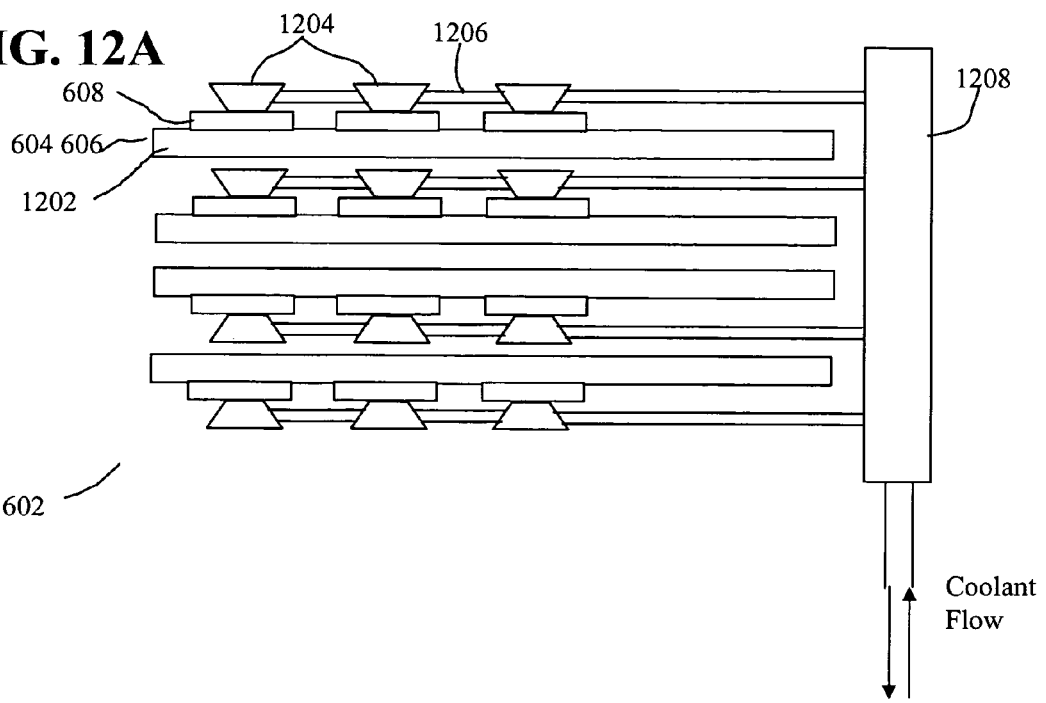
FIGS. 12A–12B depicts exemplary electronics subassemblies and electronics assemblies using liquid cooling for use with the embodiment of FIG. 6.
Figure 12B:
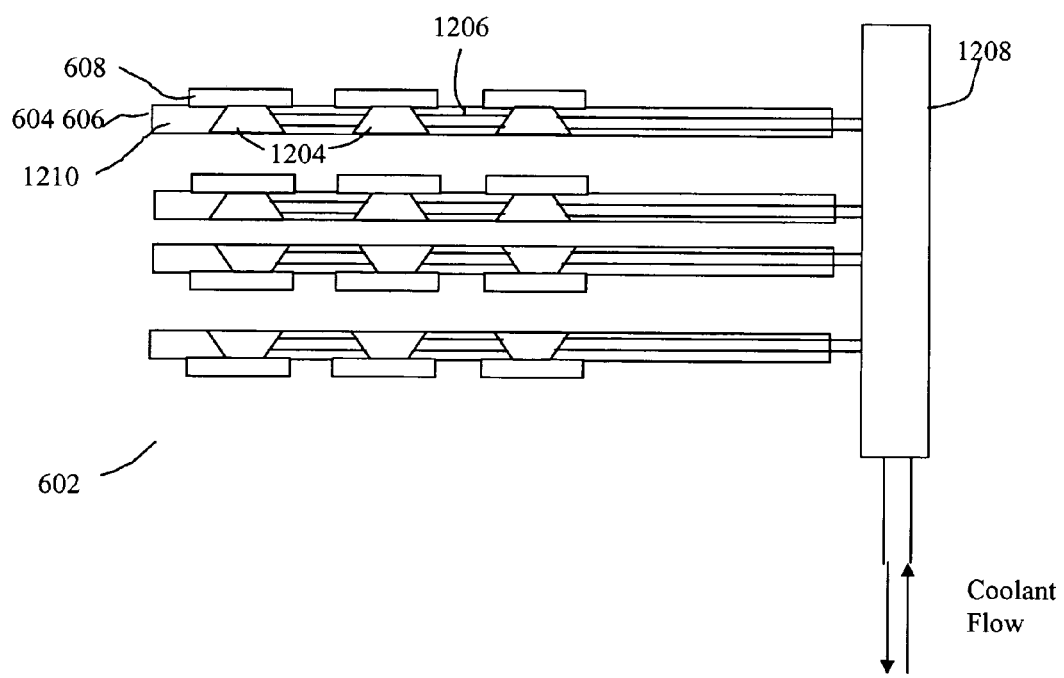

In another embodiment shown in FIG. 12A, thermal energy is conducted out of the assembly 602 by active cooling means, such as by circulating a coolant within a path directly on or within the PCB 1202. In particular where the piezoelectric transducer module, also referred to as the "acoustic module", is actively liquid cooled, the same coolant that is used to actively remove heat from the piezoelectric transducer module would be distributed in a manifold 1208 and would pass near by the heat generating components 608 on the PCB, removing heat from within the assembly 602. In one embodiment, one or more liquid cooled heat exchangers 1204 are affixed to, or proximate to, each heat generating component 608 on the sub-assembly 604 606 prior to assembly. Further, coolant tubes 1206 are connected with these heat exchangers 1204. Upon assembly of the electronics assembly 602, the coolant tubes 1206 are interconnected with the manifold 1208 to as to allow coolant to circulate into the assembly 602 and remove thermal energy therefrom. In an alternative embodiment, shown in FIG. 12B, the heat exchangers 1204 and coolant tubes 1206 are embedded in the printed circuit board 1210 upon manufacture.

In yet another embodiment, not shown, the entire electronics assembly 602 is encapsulated within a sealed container. This container could be the transducer handle housing or a structure within the transducer handle housing. Within this container a thermally conductive and electrically insulating fluid, such as Fluorinert™ manufactured by 3M, located in St. Paul, Minn., is provided which may be used to transfer heat from the heat generating components 608 to an integrated heat sink that is actively cooled by a separate coolant flowing within a heat exchanger.

A design problem that arises, as a result of raising the transducer housing temperature with heat generating electronics, is that the traditional cooling path for the transducer module is made much less efficient. The transducer module may be a piezoelectric based transducer module, micromechanical based transducer module, or a different technology, or combination thereof. The temperature differential between the lens of the operating transducer assembly and the transducer handle is greatly reduced, potentially leading to the lens temperature being driven beyond regulatory limits. As described above, a Peltier or other thermoelectric device may be used to drive down the reference sink temperature for the transducer module. While the inefficiency of a Peltier device may consume more power and generate more heat than can be easily dissipated in a passive cooling design, in an actively cooled transducer this inefficiency is only an incremental increase to the total thermal load. As was described above, the Peltier device 902 may be thermally attached to the backer, the signal conductors, grounds and shields, or a thermal structure specifically designed to be an isothermal structure around the transducer module 904, as shown in FIGS. 9A and 9B. In order to thermally manage the entire transducer, including both the transducer module 904 and the electronics assemblies 602, in one embodiment, the hot side of the Peltier device 902may be attached to a sufficiently thick strip of highly thermally conductive material 906. As described above, the transducer module 904 may include a piezoelectric based transducer module, micro-mechanical based transducer module, or a different technology, or combination thereof. The other end of the thermally conductive strip 906 may be attached to the active cooling heat exchanger 908 that is used to cool the transducer electronics assembly 602, which is coupled with the heat exchanger 908 as described above. In another embodiment, a heat pipe 910 may be used to transfer the heat from a heat exchanger 912 contacting the hot side of the Peltier device 902 to the active heat exchanger 908, as shown in FIG. 9B. A third embodiment may continue the active cooling coolant loop 1012 from the electronics assembly 602 heat exchanger 908 and redirect it to the Peltier device 902 heat exchanger 1012 to pull away heat from the hot side before the coolant completes its cooling cycle, as shown in FIG. 10A.

In another embodiment, the Peltier device 1018 may be located between the transducer module 904 and the active cooling heat exchanger 1020 to the other side of the heat exchanger 1020, as shown in FIG. 10B. This drives down the temperature of the electronics assembly 602 but places a large burden on the entire cooling system due to inefficiencies of the Peltier device 1018. In this case, the transducer module 904 may be attached to the electronics assembly 602 heat sink 1022 via a solid conductor or a heat pipe 1016.

So as not to disrupt the thermal control of different portions of the transducer, electronics assemblies 602 and transducer modules 904 included in the same transducer handle may be thermally isolated from one another to control the specific heat dissipation paths for the two heat sources. The thermal paths may be adjusted by tuning the thermal conductivity or thickness of the insulation around the heat sources. By controlling the heat paths, one may fine tune the thermal profile of the transducer handle to maximize the efficiency of the thermal design.

Figures 11A, 11B, 11C:
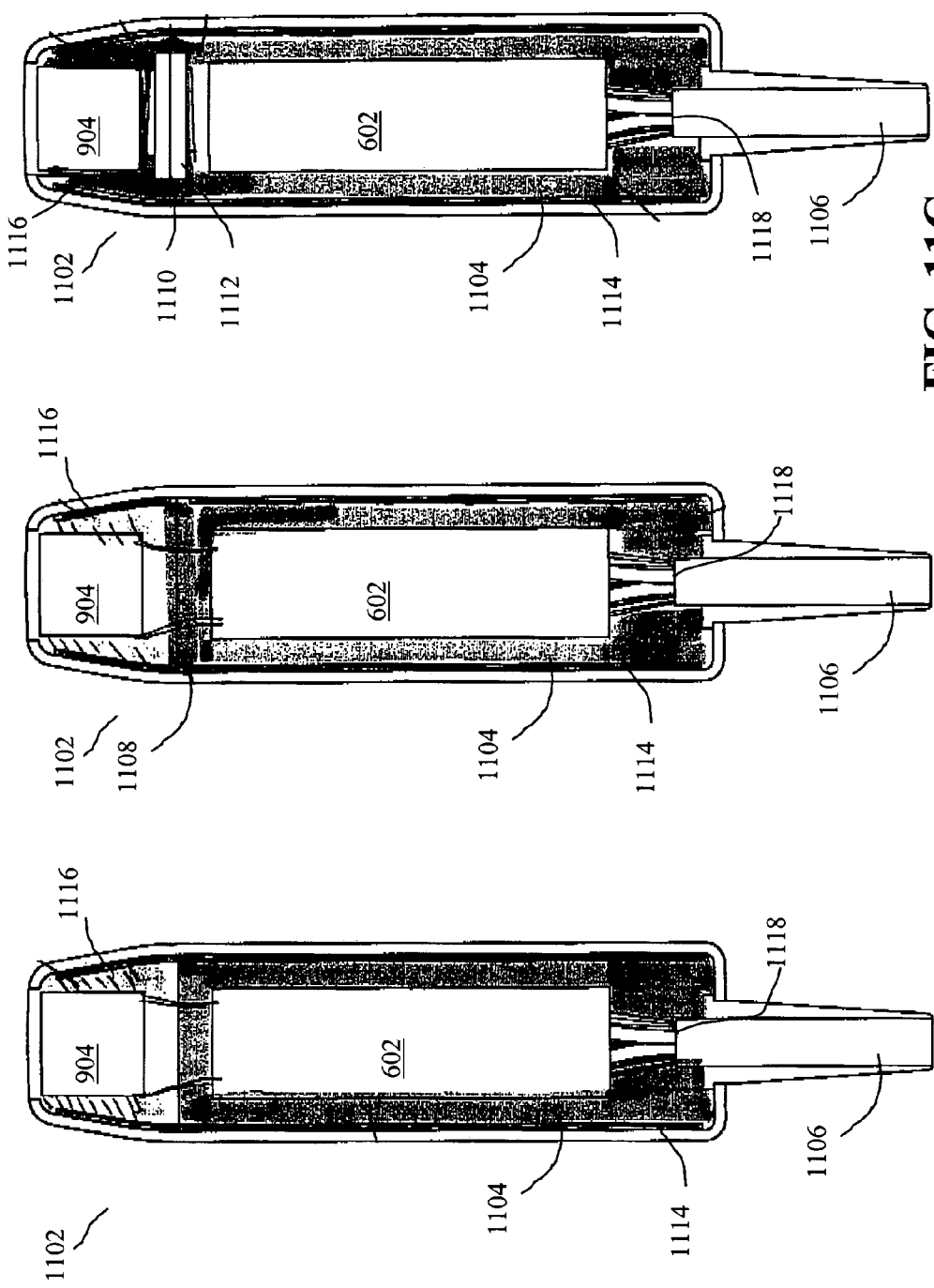
FIGS. 11A–11C depict thermal isolation of the transducer module and electronics assembly according to one embodiment.

As shown in FIG. 11A, an extremely low thermal conductivity insulator 1104 surrounds the electronics assembly(s) 602 in the handle 1102. This may be accomplished in many ways including, but not limited to, polyurethane foam, syntactic foam, a Gore-tex wrap, an adequately spaced air-gap or a vacuum gap built into the handle 1102 housing plastic. When the electronics assemblies 602 are well insulated, nearly all of the heat generated within the electronics is pulled away down the cable 1106 by the active cooling means, described above. The transducer handle 1102 temperature is therefore not raised significantly by the electronics. This allows transducer module 904 to utilize the entire surface of the handle 1102 as a convection and/or radiation surface as would be the case in a transducer without heat generating electronics.

Figure 1:
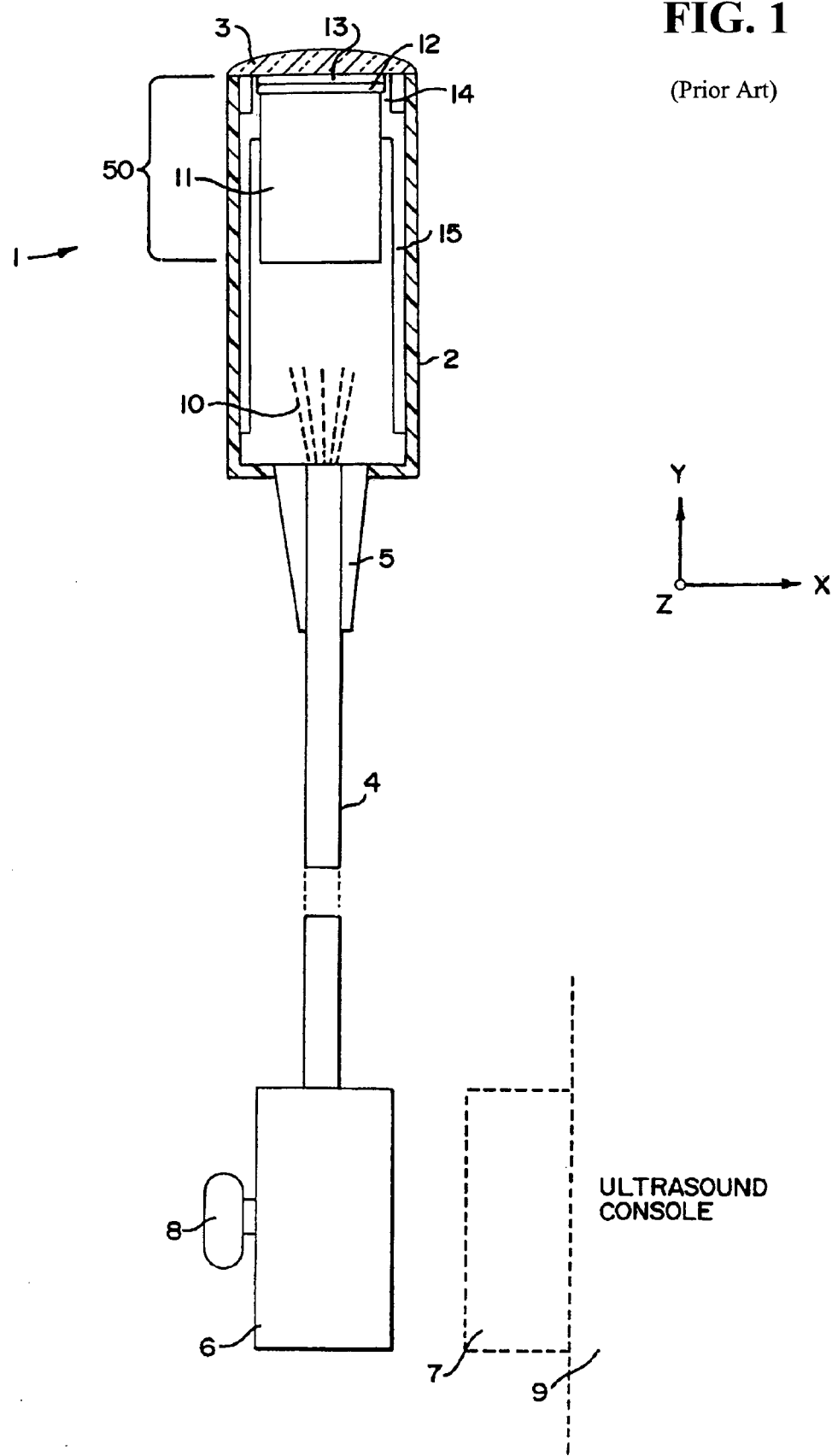
FIG. 1 depicts a partial cross-sectional view of a typical industry-standard, solid-state, phased array transducer with its accompanying cable, system connector, system-console, mating connector, and typical passive heat distribution plates.
Figure 2:
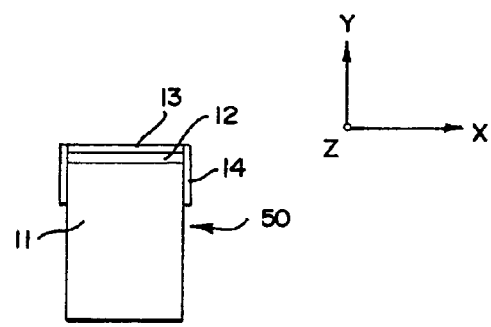
FIG. 2 depicts a side view of a piezoelement transducer assembly of the type used in the device shown in FIG. 1.

In some cases it might be desirable to use a portion of the transducer handle as a convection and/or radiant surface for the heat generated by the electronics assemblies 602. FIG. 1B depicts a case where the amount of insulating material 1104 in the handle 1102 has been tuned to allow the case to reach a specific temperature range during normal use. A portion of the heat generated by the electronics assembly(s) 602is dissipated by this handle 1102 surface and the balance is pulled away down the cable 1106 by the active cooling means, as described. Similarly there is a portion of the transducer handle 1102 specifically designed for dissipation of heat generated within the transducer module 1102. The two heat sources and thermal paths are thermally isolated by a very good thermal insulator 1108.

Both the designs above could be used with Peltier devices (not shown) implemented at either the transducer module 904 or the electronics assembly 602 or both, as described in detail above.

In another embodiment shown in FIG. 11C, the transducer module 904 may be cooled by a Peltier device 1110 and could be well insulated from the rest of the transducer handle by the same methods described above and shown in FIG. 11B. The hot side 1112of the Peltier device 1110 is on the electronics assembly 602 side of the insulating barrier 1108. The insulation surrounding the Peltier device 1110 and electronics assembly 602 is tuned to drive the transducer handle 1102 to a specific temperature range. The balance of the heat generated by the Peltier device 1110 and the electronics assembly 602 is carried down the cable 1196 by active means, or otherwise dissipated as described above.

It will be appreciated that the disclosed embodiments are not limited to one dimensional transducers and may be used with 2-D or other types of transducers as well.

It is therefore intended that the foregoing detailed description be regarded as illustrative rather than limiting, and that it be understood that it is the following claims, including all equivalents, that are intended to define the spirit and scope of this invention. the thermoelectric cooler.

We claim:

1. An ultrasound transducer, comprising:
   a housing;
   a transducer module mounted in said housing, said transducer module operable to transmit ultrasonic energy; and
   an electronics assembly located in said housing and coupled with said transducer and characterized by an interior portion and an exterior portion, said electronics assembly including:
   at least two electronics sub-assemblies each having at least one discrete electrical component affixed thereto, said at least one discrete electrical component having a heat conductive surface and wherein said at least one discrete electrical component of at least one of said at least two electronics sub-assemblies is located in said interior portion such that said heat conductive surface of said at least one discrete electrical component of said at least one of said at least two electronics sub-assemblies faces the other of the at least two electronics sub-assemblies; and
   a first thermal conductor thermally coupled with said heat conductive surface of said at least one discrete electrical component of said at least one of said at least two electronics sub-assemblies and operable to remove heat generated by said at least one discrete electrical component and move said heat from said interior portion to said exterior portion.

2. The ultrasound transducer of claim 1, further comprising a second thermal conductor coupled with said first thermal conductor and located proximate to said exterior portion and operative to remove said heat from said first thermal conductor.

3. The ultrasound transducer of claim 2, wherein said second thermal conductor further comprises a thermoelectric cooler.

4. The ultrasound transducer of claim 3, wherein said thermoelectric cooler comprises a Peltier device.

5. The ultrasound transducer of claim 2, wherein said second thermal conductor is coupled with said transducer module and further operative to remove heat generated by said transducer module.

6. The ultrasound transducer of claim 5, wherein said second thermal conductor is coupled with said transducer module by a solid thermal conductor.

7. The ultrasound transducer of claim 5, wherein said second thermal conductor is coupled with said transducer module by a liquid thermal conductor.

8. The ultrasound transducer of claim 1, wherein said first thermal conductor further comprises at least one thermally conductive sheet disposed over said at least one discrete component and extending from said interior portion to said exterior portion of said electronics assembly.

9. The ultrasound transducer of claim 8, wherein said at least one thermally conductive sheet is coupled with at least one other thermally conductive sheet and a second thermal conductor by a thermally conductive connector.

10. The ultrasound transducer of claim 1, wherein said at least one of said at least two electronics sub-assemblies further comprises a printed circuit board, said printed circuit board comprising said first thermal conductor.

11. The ultrasound transducer of claim 1, wherein said first thermal conductor comprises at least one heat pipe.

12. The ultrasound transducer of claim 1, wherein said first thermal conductor comprises a liquid cooling loop.

13. The ultrasound transducer of claim 12, wherein said at least one of said at least two electronics sub-assemblies further comprises a printed circuit board, said liquid cooling loop being embedded in said printed circuit board.

14. The ultrasound transducer of claim 1, wherein said housing further comprises a transducer portion housing said transducer module and an electronics portion housing said electronics assembly, said housing further comprising a thermal separator operative to thermally isolate said transducer portion from said electronics portion.

15. The ultrasound transducer of claim 14, wherein said thermal separator comprises a thermoelectric cooler, said thermoelectric cooler having a cold side located in said transducer portion and operative to remove heat from said transducer, and a hot side located in said electronics portion.

16. The ultrasound transducer of claim 1, wherein said transducer module comprises a micro-mechanical based transducer.

17. A method of cooling an ultrasound transducer, said ultrasound transducer comprising a housing, a transducer module mounted in said housing and an electronics assembly located in said housing and characterized by an interior portion and an exterior portion, said electronics assembly including at least two electronics sub-assemblies each having at least one discrete electrical component affixed thereto, said at least one discrete electrical component having a heat conductive surface and wherein the at least one discrete electrical component is located in said interior portion such that said heat conductive surface of said at least one discrete electrical component of said at least one of said at least two electronics sub-assemblies faces the other of the at least two electronics sub-assemblies, said method comprising:
   generating heat by said at least one discrete electrical component; and
   removing said heat from said interior portion to said exterior portion using a first thermal conductor thermally coupled with said heat conductive surface of said at least one discrete electrical component of said at least one of said at least two electronics sub-assemblies.

18. The method of claim 17, wherein said removing said heat from said first thermal conductor further comprises actively conducting said heat away from said first thermal conductor using a thermoelectric cooler.

19. The method of claim 17, further comprising disposing at least one thermally conductive sheet over said at least one discrete component and extending said at least one thermally conductive sheet from said interior portion to said exterior portion of said electronics assembly.

20. The method of claim 17, wherein said at least one of said at least two electronics sub-assemblies comprises a printed circuit board coupled with said at least one discrete electrical component, said method further comprising embedding said first thermal conductor in said printed circuit board.

21. The method of claim 17, wherein said first thermal conductor comprises at least one heat pipe.

22. The method of claim 17, wherein said first thermal conductor comprises a liquid cooling loop.

23. The method of claim 22, wherein said at least one of said at least two electronics sub-assemblies further comprises a printed circuit board, said liquid cooling loop being embedded in said printed circuit board.

24. The method of claim 17 further comprising:
   removing said heat from said first thermal conductor by a second thermal conductor located proximate to said exterior portion and coupled with said first thermal conductor.

25. The method of claim 24, wherein said second thermal conductor is further coupled with said transducer module, said method further comprising removing heat generated by said transducer module by said second thermal conductor.

26. The method of claim 25, wherein said second thermal conductor is coupled with said transducer module by a solid thermal conductor.

27. The method of claim 25, wherein said second thermal conductor is coupled with said transducer module by a liquid thermal conductor.

28. The method of claim 17, wherein said housing further comprises a transducer portion housing said transducer module and an electronics portion housing said electronics assembly, said method further comprising thermally isolating said transducer portion from said electronics portion.

29. The method of claim 28, further comprising thermally isolating said transducer portion from said electronics portion using a thermoelectric cooler, said thermoelectric cooler having a cold side located in said transducer portion and operative to remove heat from said transducer, and a hot side located in said electronics portion.

30. An ultrasound transducer comprising:
a housing;
a transducer module mounted in said housing; and
an electronics assembly located in said housing and characterized by an interior portion and an exterior portion, said electronics assembly including at least two electronics sub-assemblies each having at least one discrete electrical component affixed thereto, said at least one discrete electrical component having a heat conductive surface and wherein said at least one discrete electrical component of at least one of said at least two electronics sub-assemblies is located in said interior portion such that said heat conductive surface of said at least one discrete electrical component of said at least one of said at least two electronics sub-assemblies faces the other of the at least two electronics sub-assemblies;
said ultrasound transducer further comprising:
means for removing heat generated by said at least one discrete electrical component from said interior portion to said exterior portion using a first thermal conductor means thermally coupled with said heat conductive surface of said at least one discrete electrical component of said at least one of said at least two electronics sub-assemblies.

31. The ultrasound transducer of claim 30 further comprising:
means for removing said heat from said first thermal conductor means by a second thermal conductor means located proximate to said exterior portion and coupled with said first thermal conductor means.

* * * * *